US010947500B2

(12) United States Patent
Qiang et al.

(10) Patent No.: US 10,947,500 B2
(45) Date of Patent: Mar. 16, 2021

(54) NEURAL CELLS EXPRESSING ADENOVIRUS E4ORF1, AND METHODS OF MAKING AND USING THE SAME

(71) Applicant: ANGIOCRINE BIOSCIENCE, INC., San Diego, CA (US)

(72) Inventors: Liang Qiang, Philadelphia, PA (US); Daniel Joseph Nolan, Hawthorne, NY (US); Claude Geoffrey Davis, Auburn, CA (US)

( * ) Notice: Subject to any disclaimer, the term of this patent is extended or adjusted under 35 U.S.C. 154(b) by 0 days.

(21) Appl. No.: 15/322,109

(22) PCT Filed: Jun. 26, 2015

(86) PCT No.: PCT/US2015/038182
§ 371 (c)(1),
(2) Date: Dec. 24, 2016

(87) PCT Pub. No.: WO2015/200897
PCT Pub. Date: Dec. 30, 2015

(65) Prior Publication Data
US 2017/0137781 A1 May 18, 2017

Related U.S. Application Data

(60) Provisional application No. 62/018,056, filed on Jun. 27, 2014.

(51) Int. Cl.
| | | |
|---|---|---|
| *C12N 5/10* | (2006.01) | |
| *C12N 5/079* | (2010.01) | |
| *C12N 15/34* | (2006.01) | |
| *C12N 15/85* | (2006.01) | |
| *C07K 14/075* | (2006.01) | |
| *A61K 48/00* | (2006.01) | |
| *C12N 5/0793* | (2010.01) | |
| *A61K 35/30* | (2015.01) | |
| *C07K 14/005* | (2006.01) | |
| *C12N 7/00* | (2006.01) | |
| *C12N 15/86* | (2006.01) | |

(52) U.S. Cl.
CPC ............ *C12N 5/0622* (2013.01); *A61K 35/30* (2013.01); *A61K 48/005* (2013.01); *C07K 14/005* (2013.01); *C12N 5/0619* (2013.01); *C12N 7/00* (2013.01); *C12N 15/86* (2013.01); *C12N 2501/998* (2013.01); *C12N 2502/081* (2013.01); *C12N 2502/086* (2013.01); *C12N 2506/00* (2013.01); *C12N 2510/00* (2013.01); *C12N 2533/90* (2013.01); *C12N 2710/10333* (2013.01)

(58) Field of Classification Search
None
See application file for complete search history.

(56) References Cited

U.S. PATENT DOCUMENTS

| | | | |
|---|---|---|---|
| 6,852,533 B1 | 2/2005 | Rafii et al. | |
| 7,241,591 B2 * | 7/2007 | Barkats | A61K 48/00 424/93.2 |
| 7,396,680 B2 | 7/2008 | Shmelkov et al. | |
| 8,465,732 B2 | 6/2013 | Rafii et al. | |
| 9,637,723 B2 | 5/2017 | Rafii et al. | |
| 2002/0028497 A1 * | 3/2002 | Blanche | B01D 15/363 435/235.1 |
| 2002/0165193 A1 * | 11/2002 | Greene | A61K 38/1709 514/44 R |
| 2010/0003757 A1 | 1/2010 | Mack et al. | |
| 2010/0093081 A1 | 4/2010 | Rafii et al. | |
| 2010/0273200 A1 | 10/2010 | Niwa et al. | |
| 2011/0027235 A1 | 2/2011 | Gregory et al. | |
| 2013/0224161 A1 | 8/2013 | Rafii et al. | |
| 2014/0348825 A1 * | 11/2014 | Friedman | B82Y 5/00 424/134.1 |
| 2015/0361398 A1 | 12/2015 | Sandler et al. | |
| 2015/0374766 A1 * | 12/2015 | O'Shea | A61K 35/761 424/93.2 |
| 2016/0008413 A1 * | 1/2016 | Fisher | A61K 39/0011 424/93.2 |

FOREIGN PATENT DOCUMENTS

| | | |
|---|---|---|
| EP | 0773287 A1 | 5/1997 |
| JP | 2001238681 A | 9/2001 |
| JP | 2013 017434 A | 1/2013 |
| WO | 2002036829 A2 | 5/2002 |
| WO | 2003103608 A2 | 12/2003 |
| WO | 2006113731 A2 | 10/2006 |
| WO | 2008039173 A2 | 4/2008 |
| WO | 2008134539 A1 | 11/2008 |

(Continued)

OTHER PUBLICATIONS

Sivasubramaniam et al, Gene delivery into neuronal and glial cells by using a replication-deficient adenovirus vector: prospects for neurological gene therapy, Cytotechnology 24: 253-259, 1997.*
Tanapat, P, Neuronal Cell Markers, Mater Methods 2013; pp. 1-10.*
Gordon-Lipkin and Fatemi, Current Therapeutic Approaches in Leukodystrophies: A Review, J Child Neurol. Nov. 2018 ; 33(13):861-868.*
Muraoka et al, The high integration and differentiation potential of autologous neural stem cell transplantation compared with allogeneic transplantation in adult rat hippocampus, Experimental Neurology 199 (2006) 311-327.*
Chiu and Rao, Cell-Based Therapy for Neural Disorders—Anticipating Challenges, Neurotherapeutics (2011) 8:744-752.*

(Continued)

*Primary Examiner* — Maria Marvich
(74) *Attorney, Agent, or Firm* — Grimes & Yvon LLP

(57) ABSTRACT

In certain aspects the present invention provides engineered neural cells, neural stem cells, or neural progenitor cells that contain a nucleotide sequence that encodes an adenovirus E4ORF1 polypeptide and/or that contain an adenovirus E4ORF1 polypeptide. The present invention also provides methods of making and using such engineered cells and compositions comprising such engineered cells.

36 Claims, 2 Drawing Sheets

(56) References Cited

FOREIGN PATENT DOCUMENTS

| WO | 2009137674 | A2 | 11/2009 |
|---|---|---|---|
| WO | 2010046710 | A1 | 4/2010 |
| WO | 2012016049 | A1 | 2/2012 |
| WO | 2012061828 | A2 | 5/2012 |
| WO | 2013144999 | A1 | 10/2013 |
| WO | 2014052835 | A1 | 4/2014 |
| WO | 2014093270 | A1 | 6/2014 |

OTHER PUBLICATIONS

Sandberg et al, Neurological disorders and the potential role for stem cells as a therapy, British Medical Bulletin 2012; 101: 163-181.*
Casarosa et al. Molecular and Cellular Therapies 2014, pp. 1-7.*
Sun and Kurtzberg, Cell therapy for diverse central nervous system disorders: inherited metabolic diseases and autism, Pediatric Research, 2018, pp. 364-371.*
Minh Thai et al: "Adenovirus E4ORF1-Induced MYC Activation Promotes Host Cell Anabolic Glucose Metabolism and Virus Replication", Cell Metabolism, vol. 19, No. 4, Apr. 1, 2014, pp. 694-701.
Takashi Nagasawa et al: "Control of hematopoietic stem cells by the bone marrow stromal niche: the role of reticular cells"; Trends in Immunology, vol. 32, No. 7, pp. 315-320.
Seandel et al: "Generation of a functional and durable vascular niche by the adenoviral E4ORF1 gene"; Proceedings of the National Academy of Sciences (PNAS), vol. 105, No. 49. pp. 19288-19293.
O'Shea et al: "Adenoviral proteins mimic nutrient/growth signals to activate the mTOR pathway for viral replication"; The EMBO Journal (2005) 24, 1211-1221.
Zhang et al: "Adenovirus E4 Gene Promotes Selective Endothelial Cell Survival and Angiogenesis via Activation of the Vascular Endothelial-Cadherin/Akt Signaling Pathway"; The Journal of Biological Chemistry (2004) vol. 279, No. 12, pp. 11760-11766.
Bridge & Ketner, "Redundant Control of Adenovirus Late Gene Expression by Early Region 4," J. Virology, Feb. 1989, p. 631-638.
Riken BRC, "RDB01727—Axl CA gfp", [online], Dec. 10, 2018, Internet <URL: https://dnaconda.riken.jp/search/RDB_clone/RDB01/RDB01727.html>.

* cited by examiner

NEURAL CELLS EXPRESSING ADENOVIRUS E4ORF1, AND METHODS OF MAKING AND USING THE SAME

CROSS-REFERENCE TO RELATED APPLICATIONS

This application is a U.S. National Stage entry under 35 U.S.C. § 371 of International Patent Application No. PCT/US2015/038182, filed Jun. 26, 2015, which claims the benefit of U.S. Provisional Patent Application No. 62/018,056, filed Jun. 27, 2014, the contents of which are here by incorporated by reference.

INCORPORATION BY REFERENCE

For the purposes of those jurisdictions that permit incorporation-by-reference only, the text of all documents cited herein is hereby incorporated by reference in its entirety.

BACKGROUND OF THE INVENTION

The adenoviral early 4 (E4) region contains at least 6 open reading frames (E4ORFs). The entire E4 region has been shown previously to regulate angiogenesis and promote survival of endothelial cells (see Zhang et al. (2004), J. Biol. Chem. 279(12):11760-66). It has also been shown previously that, within the entire E4 region, it is the E4ORF1 sequence that is responsible for these biological effects in endothelial cells. See U.S. Pat. No. 8,465,732. See also Seandel et al. (2008), "Generation of a functional and durable vascular niche by the adenoviral E4ORF1 gene," PNAS, 105(49):19288-93. However, to the best of Applicants' knowledge, prior to the present invention, there was no evidence to suggest that the adenovirus E4 region, and in particular the E4ORF1 sequence, might have beneficial effects on either neuronal cells or glial cells.

SUMMARY OF THE INVENTION

The present invention derives, in part, from the surprising discovery that expression of adenovirus E4ORF1 sequences can have certain beneficial effects in neuronal cells and glial cells—which are referred to collectively herein as neural cells. For example, it has been found that glial cells that express adenovirus E4ORF1 exhibit increased proliferation rates and can be passaged in vitro for a greater number of population doublings as compared to glial cells that do not express E4ORF1. Similarly, it has been found that neuronal cells that express adenovirus E4ORF1 exhibit increased axon length, increased numbers of minor processes, and increased numbers of branches per axon as compared to neuronal cells that do not express E4ORF1. These effects were achieved without any apparent de-differentiation or transformation of the neural cells—the E4ORF1-expressing neuronal and glial cells continued to express certain cell-type specific markers and maintained the cellular morphology characteristic of their cell type. Building on these findings, in some embodiments the present invention provides novel methods for obtaining, maintaining, or culturing neural cells without transforming the cells or otherwise disrupting the cells' normal phenotypic characteristics and/or lineage identity. Similarly, in other embodiments the present invention provides novel engineered neural cells that may be useful in a variety of settings, including, but not limited to, therapeutic applications. For example, it is believed that the ability to increase axon length and numbers of minor processes and axon branches in neurons may provide benefits in therapeutic applications involving neuronal regeneration and/or repair. Similarly, it is believed that the ability to generate larger numbers of glial cells or glial cells having higher proliferation rates may also provide benefits in therapeutic applications involving glial regeneration and/or repair. These and other aspects of the present invention are described in more detail below and throughout the present disclosure.

In some embodiments the present invention provides populations of engineered neural cells that comprise a nucleic acid sequence that encodes an adenovirus E4ORF1 polypeptide (or a variant, derivative, mutant, fragment, or peptidomimetic thereof—as described and defined in the "Detailed Description" of the present disclosure), or populations of engineered neural cells that comprise an adenovirus E4ORF1 polypeptide (or a variant, derivative, mutant, fragment, or peptidomimetic thereof). In some such embodiments the neural cells are neuronal cells. In other such embodiments the neural cells are glial cells. In other embodiments the present invention provides populations of engineered neural stem or progenitor cells that comprise a nucleic acid sequence that encodes an adenovirus E4ORF1 polypeptide (or a variant, derivative, mutant, fragment, or peptidomimetic thereof), or populations of engineered neural stem or progenitor cells that comprise an adenovirus E4ORF1 polypeptide (or a variant, derivative, mutant, fragment, or peptidomimetic thereof). In some such embodiments the neural stem or progenitor cells are neuronal progenitor cells. In other such embodiments the neural stem or progenitor cells are glial progenitor cells. In some embodiments the populations of engineered neural cells (or populations of engineered neural stem or progenitor cells) are isolated cell populations. In some embodiments the populations of engineered neural cells (or populations of engineered neural stem or progenitor cells) are substantially pure cell populations. In some embodiments the populations of engineered neural cells (or populations of engineered neural stem or progenitor cells) are present in vitro, for example in cell culture. In some embodiments the populations of engineered neural cells (or populations of engineered neural stem or progenitor cells) are present in vivo, for example in a living subject.

In some embodiments the present invention provides compositions comprising the populations of engineered neural cells (or engineered neural stem or progenitor cells) described herein. Such compositions may comprise a carrier solution, such as a physiological saline solution. In some embodiments such compositions may be therapeutic compositions—comprising a population of engineered neural cells (or engineered neural stem or progenitor cells) and a carrier solution suitable for administration to a subject, such as a human subject.

The cell populations, and compositions comprising such cell populations, described herein may be useful in a variety of applications (as described further on other sections of this patent disclosure). In general, the engineered neural cells and neural stem or progenitor cells provided herein can be used for any application in which non-engineered (i.e. non-E4OFR1-expressing) neural cells or neural stem or progenitor cells are currently used or could be used, including, but not limited to, basic scientific research applications, cell culture methods (including neuronal/glial co-culture methods), model systems for neural diseases, tissue model systems (such as blood brain barrier model systems), target discovery, drug discovery, and drug efficacy, toxicity, and/or safety testing. For example, in some embodiments the engineered neural cells (or engineered neural stem or progenitor cells) may be useful in therapeutic applications, including, but not limited to, in vivo cell transplantation procedures.

In some embodiments the present invention provides various methods that involve expression of a nucleic acid sequence that encodes an adenovirus E4ORF1 polypeptide (or a variant, derivative, mutant or fragment thereof) in neural cells, or delivery of an adenovirus E4ORF1 polypeptide (or a variant, derivative, mutant, fragment, or peptidomimetic thereof) to neural cells. In some such embodiments the neural cells are neuronal cells. In other such embodiments the neural cells are glial cells. In other embodiments the present invention provides methods that involve expression of a nucleic acid sequence that encodes an adenovirus E4ORF1 polypeptide (or a variant, derivative, mutant, fragment, or peptidomimetic thereof) in neural stem or progenitor cells, or delivery of an adenovirus E4ORF1 polypeptide (or a variant, derivative, mutant, fragment, or peptidomimetic thereof) to neural stem or progenitor cells. In some embodiments the neural stem or progenitor cells may be neuronal stem or progenitor cells. In other embodiments the neural stem or progenitor cells may be glial stem or progenitor cells. In some embodiments the neural cells (or neural stem or progenitor cells) are isolated cells. In some embodiments the neural cells (or neural stem or progenitor cells) are substantially pure cell populations. In some embodiments the neural cells (or neural stem or progenitor cells) are present in vitro, for example in cell culture. In some embodiments the neural cells (or neural stem or progenitor cells) are present in vivo, for example in a living subject.

For example, in one embodiment the present invention provides a method of producing a population of engineered neural cells (or engineered neural stem or progenitor cells), the method comprising: introducing a nucleic acid molecule encoding an adenovirus E4ORF1 protein (or a variant, derivative, mutant, fragment, or peptidomimetic thereof) into one or more neural cells (or neural stem or progenitor cells) to produce engineered neural cells (or engineered neural stem or progenitor cells), wherein the engineered neural cells (or engineered neural stem or progenitor cells) express the E4ORF1 polypeptide. In another embodiment the present invention provides a method of obtaining a population of engineered neural cells (or neural stem or progenitor cells) in vitro, the method comprising: (a) introducing a nucleic acid molecule encoding an adenovirus E4ORF1 protein (or a variant, derivative, mutant, fragment, or peptidomimetic thereof) into one or more neural cells (or neural stem or progenitor cells) to produce engineered neural cells (or engineered neural stem or progenitor cells), wherein the engineered neural cells (or engineered neural stem or progenitor cells) express the E4ORF1 polypeptide, and (b) culturing the engineered neural cells (or engineered neural stem or progenitor cells) in vitro. Similarly, in another embodiment the present invention provides a method for culturing neural cells (or neural stem or progenitor cells), the method comprising: (a) obtaining a population of engineered neural cells (or neural stem or progenitor cells), wherein the engineered neural cells (or engineered neural stem or progenitor cells) express an E4ORF1 polypeptide (or a variant, derivative, mutant, fragment, or peptidomimetic thereof), and (b) culturing the engineered neural cells (or engineered neural stem or progenitor cells). In yet another embodiment the present invention provides a method for culturing neural cells (or neural stem or progenitor cells), the method comprising: (a) obtaining one or more neural cells (or neural stem or progenitor cells), (b) introducing a nucleic acid molecule encoding an adenovirus E4ORF1 protein (or a variant, derivative, mutant, fragment, or peptidomimetic thereof) into the one or more neural cells (or neural stem or progenitor cells) to produce engineered neural cells (or engineered neural stem or progenitor cells), wherein the engineered neural cells (or engineered neural stem or progenitor cells) express the E4ORF1 polypeptide, and (c) culturing the engineered neural cells (or engineered neural stem or progenitor cells). In yet another exemplary embodiment the present invention provides a method comprising: (a) introducing a nucleic acid molecule encoding an adenovirus E4ORF1 protein (or a variant, derivative, mutant, fragment, or peptidomimetic thereof) into one or more neural stem or progenitor cells to form engineered neural stem or progenitor cells, and (b) differentiating the one or more engineered neural stem or progenitor cells in order to produce engineered neural cells, wherein the engineered neural cells expresses the E4ORF1 protein. In yet another exemplary embodiment the present invention provides a method comprising: (a) obtaining a population of engineered neural stem or progenitor cells that express an adenovirus E4ORF1 protein (or a variant, derivative, mutant, fragment, or peptidomimetic thereof), and (b) differentiating the one or more engineered neural stem or progenitor cells in order to produce engineered neural cells, wherein the engineered neural cells express the E4ORF1 protein. In yet another exemplary embodiment the present invention provides a method comprising: (a) obtaining a population of neural stem or progenitor cells, (b) introducing a nucleic acid molecule encoding an adenovirus E4ORF1 protein (or a variant, derivative, mutant, fragment, or peptidomimetic thereof) into one or more neural stem or progenitor cells to form engineered neural stem or progenitor cells, and (c) differentiating the one or more engineered neural stem or progenitor cells in order to produce engineered neural cells, wherein the engineered neural cells express the E4ORF1 protein.

These and other embodiments of the invention are described further in the other sections of this patent disclosure. In addition, as will be apparent to those of skill in the art, certain modifications and combinations of the various embodiments described herein fall within the scope of the present invention.

DETAILED DESCRIPTION

Figure 1:
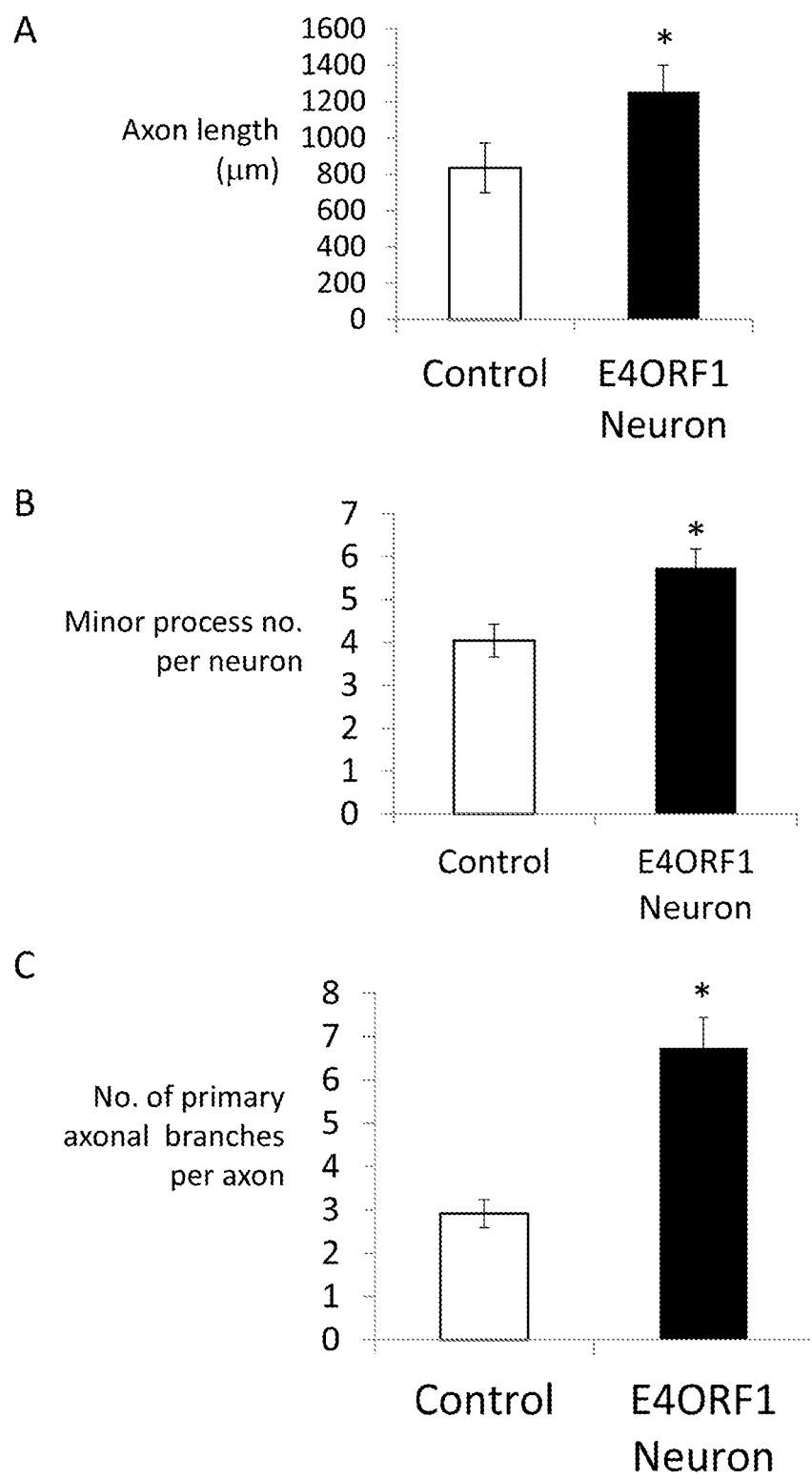
FIG. 1. Graphs showing the effects of E4ORF1 expression on axon length (FIG. 1A), number of minor processes per neuron (FIG. 1B), and number of primary axonal branches per axon (FIG. 1C) in hippocampal neurons. Data was obtained following transduction with either E4ORF1 plus GFP ("E4ORF1") or GFP alone ("Control"). The "*" symbol represents statistical significance ($p<0.05$). E4ORF1-expressing hippocampal neurons exhibited a statistically-significant increase in axon length, number of minor processes per neuron, and number of primary axonal branches per axon as compared to controls.

The "Summary of the Invention," "Figures," "Brief Description of the Figures," "Examples," and "Claims"

sections of this patent disclosure describe some of the main embodiments of the invention. This "Detailed Description" section provides certain additional description relating to the compositions and methods of the present invention, and is intended to be read in conjunction with all other sections of this patent disclosure. Furthermore, and as will be apparent to those in the art, the different embodiments described throughout this patent disclosure can be, and are intended to be, combined in various different ways. Such combinations of the specific embodiments described herein are intended to fall within the scope of the present invention.

I. DEFINITIONS

Certain definitions are provided below. Other terms are either defined elsewhere in this patent disclosure, have a meaning that is clear from the context in which they are used, or are used in accordance with their usual meaning in the art.

As used herein, the terms "about" and "approximately," when used in relation to numerical values, mean within + or −20% of the stated value.

As used herein the term "control" as used as an adjective or noun to describe cells or a cell group cells (e.g. control cells, control cell group, etc.) is used in accordance with its established scientific meaning. For example, several embodiments of the invention involve comparisons between "engineered" and "control" cells. In those embodiments, the "engineered" cells typically contain a nucleotide sequence that encodes an adenovirus E4ORF1 polypeptide or an adenovirus E4ORF1 polypeptide, while the "control" cells do not comprise a nucleotide sequence that encodes an adenovirus E4ORF1 polypeptide or an adenovirus E4ORF1 polypeptide but are otherwise comparable to the "engineered" cells in that they are cells of the same type as the "engineered" cells (e.g. if the engineered cells are astrocytes, the control cells should also be astrocytes) and are treated comparably (or essentially identically or identically) to the "engineered" cells—in accordance with standard scientific practice. For example the engineered cells and control cells should be handled and/or cultured in a comparable way, or in an essentially identical way. In some embodiments the control cells may comprise the population of cells from which the engineered cells were derived—for example the control cell group may comprise the starting cell population (for example prior to transduction with an E4ORF1 sequence) which was subsequently engineered to produce the engineered cells, for example by transduction with an E4ORF1 sequence. In other embodiments the control cells may not comprise the starting cell population from which the engineered cells were derived, but may instead comprise a different population of cells of the same type as the engineered cells.

The term "culturing" as used herein, refers to the propagation of cells on or in media of various kinds. "Co-culturing" refers to the propagation of two or more distinct types of cells on or in media of various kinds, for instance, in some embodiments, neuronal cells and glial cells may be co-cultured.

The terms "E4ORF1" and "adenovirus E4ORF1," as used herein, refer to open-reading frame 1 (or "ORF1") of the adenoviral early 4 ("E4") genomic region—further details of which are provided below. Unless specifically stated otherwise, references to "E4ORF1" or "adenovirus E4ORF1" may relate to nucleotide sequences that encode an "E4ORF1" protein/polypeptide or an "E4ORF1" protein/polypeptide. In each of the embodiments provided herein that involve an "E4ORF1" nucleotide sequence or polypeptide, such embodiments can also be carried out using a variant, derivative, mutant, fragment, or peptidomimetic of such nucleotide sequences or polypeptides—provided that such a variant, derivative, mutant, fragment, or peptidomimetic has, or retains, one or more of the functional properties described herein (which include, but are not limited to, an ability to increase cell proliferation when expressed in glial cells, and an ability to increase axonal length when expressed in neuronal cells). Further descriptions and definitions relating to E4ORF1 are provided below.

As used herein the term "effective amount" refers to an amount of a specified agent or cell population (e.g. an E4ORF1 nucleic acid molecule or vector, or a population of E4ORF1-expressing neural cells), as described herein, that is sufficient to achieve a detectable and positive effect on one or more of the desirable outcomes described herein. For example, in the case of expression of E4ORF1 in glial cells, an effective amount of an E4ORF1 nucleotide sequence (e.g. in a vector) or an E4ORF1 polypeptide to be introduced/delivered to the glial cells may be one that results in a detectable increase in the glial cells' proliferation rate as compared to that of control (non-E4ORF1-expressing) cells. Similarly, in the case of expression of E4ORF1 in neuronal cells, an effective amount of an E4ORF1 nucleotide sequence (e.g. in a vector) or an E4ORF1 polypeptide to be introduced/delivered to the neuronal cells may be one that results in a detectable increase in the neuronal cells' axonal length as compared to that of control (non-E4ORF1-expressing) cells. In the case of methods that involve administering E4ORF1 nucleotide sequences (e.g. in a vector), E4ORF1 polypeptides, or E4ORF1-expressing neural cells to a subject, an effective amount to be administered to the subject may be one that results in a detectable improvement of one or more desired biological or therapeutic indicators, (such as, for example, improved neuronal regeneration, improved remyelination, etc.), for example as compared to that of controls without E4ORF1. An appropriate "effective amount" in any individual case may be determined empirically, for example using standard techniques known in the art, such as dose escalation studies, and may be determined taking into account such factors as the planned use, the planned mode of delivery/administration, desired frequency of delivery/administration, etc. Furthermore, an "effective amount" may be determined using assays such as those described in the Examples section of this patent disclosure to assess effects on various neuronal and glial cell phenotypic characteristics.

The term "engineered" when used in relation to cells herein refers to cells that have been engineered by man to express an adenovirus E4ORF1 nucleotide sequence or an E4ORF1 polypeptide. The term "engineered cells" is not intended to encompass any naturally occurring cells, but is, instead, intended to encompass cells that are the result of the introduction into cells of recombinant nucleotide sequences that encode an adenovirus E4ORF1 polypeptide. Additional details regarding suitable recombinant nucleotide sequences that can be used to generate such engineered cells are provided below—for example in relation to suitable E4ORF1 sequences (e.g. cDNAs), suitable vectors, suitable promoters, and the like.

The terms "expansion" or "expanding" as used herein in the context of cells or cell culture refer to an increase in the number of cells of a certain type (for example glial cells or neuronal cells) from an initial population of cells, which may or may not be identical. The initial cells used for expansion need not be the same as the cells generated as a result of the expansion. For instance, the expanded cells may be produced by growth and differentiation of the initial population of cells.

"Genetic modification" or "gene-modified" refers to any addition, deletion or disruption of or to a cell's normal nucleotide sequences. In some embodiments, the neural cells described herein may, in addition to containing and/or expressing an E4ORF1 sequence, may also comprise one or more other genetic modifications—as desired. The term "genetic modification" encompasses use of a gene delivery vehicle and includes, but is not limited to, transduction (viral mediated transfer of nucleic acid to a recipient, either in vivo or in vitro), transfection (uptake by cells of isolated nucleic acid), liposome mediated transfer and others means well known in the art.

As used herein the term "isolated" refers to a product, compound, or composition which is separated from at least one other product, compound, or composition with which it is associated in its naturally occurring state, whether in nature or as made synthetically.

The terms "subject" and "patient" are used herein interchangeably and refer to, except where indicated, mammals such as humans and non-human primates, as well as rabbits, rats, mice, goats, pigs, and other mammalian species.

The phrase "substantially pure" as used herein in relation to a cell population refers to a population of cells of a specified type (e.g. as determined by expression of one or more specified cell markers, morphological characteristics, or functional characteristics), or of specified types (plural) in embodiments where two or more different cell types are used together, that is at least about 50%, preferably at least about 75-80%, more preferably at least about 85-90%, and most preferably at least about 95% of the cells making up the total cell population. Thus, a "substantially pure cell population" refers to a population of cells that contain fewer than about 50%, preferably fewer than about 20-25%, more preferably fewer than about 10-15%, and most preferably fewer than about 5% of cells that are not of the specified type or types.

II. E4ORF1

In each of the embodiments of the present invention that involve or recite an E4ORF1 nucleic acid sequence or an E4ORF1 polypeptide, the E4ORF1 sequence used may comprise the whole adenovirus E4ORF1 sequence, or a derivative, variant, mutant, fragment or peptidomimetic thereof that has one or more of the functional properties described herein (for example, but not limited to, the ability to increase cell proliferation in glial cells or the ability to increase axon length in neurons). Adenovirus E4ORF1 sequences are known in the art and any such sequence can be used in accordance with the present invention. For example, the sequence of the human adenovirus type 5 E4 region (containing ORF1) is available on Genbank (see for example accession number D12587). In one embodiment of the invention, the E4ORF1 sequence used is that of human adenovirus type 5, which is well known in the art, or a sequence with greater than 85% sequence identity to the E4ORF1 sequence of human adenovirus type 5. In another embodiment, the variant or mutant of the E4ORF1 sequence is a sequence with about an 85% identity to the E4ORF1 sequence of human adenovirus type 5, or about an 88%, 89%, 90%, 91%, 92%, 93%, 94%, 95%, 96%, 97%, 98%, or 99% sequence identity to the E4ORF1 sequence of human adenovirus type 5 that retains the ability to promote the survival and proliferation of the various cells described herein. In another embodiment, a fragment of the E4ORF1 is a sequence which varies in length by +−.30 nucleotides relative to the E4ORF1 sequence of human adenovirus type 5, or about .+−.28 nucleotides, .+−.26 nucleotides, .+−.24 nucleotides, .+−.22 nucleotides, .+−.20 nucleotides, .+−.18 nucleotides, .+−.16 nucleotides, .+−.14 nucleotides, .+−.12 nucleotides, .+−0.10 nucleotides, .+−.9 nucleotides, .+−.8 nucleotides, .+−.7 nucleotides, .+−.6 nucleotides, .+−.5 nucleotides, .+−.4 nucleotides, .+−.3 nucleotides, .+−.2 nucleotides, or .+−.1 nucleotides relative to the E4ORF1 sequence of human adenovirus type 5, all of which may retain the properties described herein, including, but not limited to, the ability to promote survival and proliferation of the various cells described herein.

Alternatively, the E4ORF1 sequence used can be, or can be derived from, other adenovirus types or strains. Examples of other adenoviral E4ORF1 sequences include, but are not limited to, those of human adenovirus 9 (Genbank Accession No. CAI05991), human adenovirus 7 (Genbank Accession No. AAR89977), human adenovirus 46 (Genbank Accession No. AAX70946), human adenovirus 52 (Genbank Accession No. ABK35065), human adenovirus 34 (Genbank Accession No. AAW33508), human adenovirus 14 (Genbank Accession No. AAW33146), human adenovirus 50 (Genbank Accession No. AAW33554), human adenovirus 2 (Genbank Accession No. AP.sub.—000196), human adenovirus 12 (Genbank Accession No. AP.sub.—000141), human adenovirus 35 (Genbank Accession No. AP.sub.—000607), human adenovirus 7 (Genbank Accession No. AP.sub.—000570), human adenovirus 1 (Genbank Accession No. AP.sub.—000533), human adenovirus 11 (Genbank Accession No. AP.sub.—000474), and human adenovirus 3 (Genbank Accession No. ABB 17792).

In some embodiments the E4ORF1 nucleic acid sequences can be used in conjunction with one or more other nucleic acid sequences from the E4 region, such as the E4ORF2, E4ORF3, E4ORF4, E4ORF5, and/or E4ORF6 sequences, or variants, mutants or fragments thereof. For example, the E4ORF1 sequence can be used in conjunction with one or more other sequences from the E4 region for the production of E4ORF1-expressing cells. In some embodiments, the E4ORF1 sequences are not in the context of the entire E4 region, or not in the context of each of the ORFs found in the entire E4 region, or not in the context of the E4ORF2, E4ORF3, E4ORF4, E4ORF5, and/or E4ORF6 regions. For example, although E4ORF1 sequences can be used in constructs (such as a viral vectors) that contain other sequences, genes, or coding regions (such as marker genes, antibiotic resistance genes, and the like), in certain embodiments, the E4ORF1 sequences are used in constructs that do not contain the entire E4 region, or that do not contain other ORFs from the entire E4 region, such as E4ORF2, E4ORF3, E4ORF4, E4ORF5 and/or E4ORF6.

The E4ORF1 sequences can be used in constructs that contain various other sequences, genes, or coding regions, depending on the desired use. For example, the E4ORF1 nucleic acid sequences can be used in conjunction with antibiotic resistance genes, reporter genes or expression tags (such as, for example, GFP), or any other sequences or genes that might be desirable to express. The E4ORF1 nucleic acid sequences can also be expressed as part of fusion proteins. The E4ORF1 sequences can also be used in conjunction with any other desired nucleic acid sequence, gene, coding region, or non-coding region that may be present in an expression construct or viral vector that is desired to be used, or with any other nucleic acid sequence, gene, coding region, or non-coding region that is desired.

In some embodiments the E4ORF1 nucleic acid sequences can be under the control of one or more promoters to allow for expression. Any promoter able to drive expression of the E4ORF1 nucleic acid sequences in the desired cell type can be used. Examples of suitable promoters include, but are not limited to, the CMV, SV40, RSV, HIV-Ltr, and MML promoters. The promoter can also be a promoter from the adenovirus genome, or a variant thereof. For example, the promoter can be the promoter used to drive expression of E4ORF1 in an adenovirus.

In some embodiments, the E4ORF1 nucleic acid sequences can be placed under the control of an inducible promoter, so that expression of the E4ORF1 nucleic acid sequences can be turned on or off as desired. Any suitable inducible expression system can be used, such as, for example, a tetracycline inducible expression system, or a hormone inducible expression system. This can be useful for in vivo applications. For example, the E4ORF1 nucleic acid sequences can be expressed while they are needed and then switched off when the desired outcome has been achieved, for example when there has been sufficient growth or proliferation of the cells expressing the E4ORF1. The ability to turn off expression of the E4ORF1 sequences could be useful for in vivo applications.

In those embodiments of the present invention that involve nucleic acid sequences encoding adenovirus E4ORF1, the nucleic acid sequence(s) can be any suitable nucleic acid sequence(s)—whether made of naturally occurring nucleotides, synthetic nucleotides, or a combination thereof. For example, in some embodiments the nucleic acid(s) can comprise RNA, such as synthetic modified RNA that is stable within cells and can be used to direct protein expression/production directly within cells. In other embodiments the nucleic acid(s) can comprise DNA. In embodiments where DNA is used, the DNA sequences encoding E4ORF1 may be operably linked to one or more suitable promoters and/or regulatory elements to allow (and/or facilitate, enhance, or regulate) expression within cells, and may be present in one or more suitable vectors or constructs. Nucleic acid sequences encoding E4ORF1 can be introduced into endothelial cells in the same nucleic acid construct or they can be introduced in separate nucleic acid constructs.

In those embodiments of the present invention that involve introducing a nucleic acid sequence encoding an adenovirus E4ORF1 polypeptide into cells, the nucleic acid sequence encoding E4ORF1 can be any suitable nucleic acid—whether made of naturally occurring nucleotides, synthetic nucleotides, or a combination thereof. For example, in some embodiments the nucleic acid(s) can comprise RNA, such as synthetic modified RNA that is stable within cells and can be used to direct protein expression/production directly within cells. In other embodiments the nucleic acid(s) can comprise DNA. In embodiments where DNA is used, the DNA sequences encoding E4ORF1 may be operably linked to one or more suitable promoters and/or regulatory elements to allow, and/or facilitate, enhance, or regulate, expression within cells, and may be present in one or more suitable vectors or constructs. The nucleic acid sequence encoding E4ORF1 can be introduced at the same time or separately (with one being introduced at one time and the other being introduced at a different time). Also the nucleic acid sequence encoding E4ORF1 can be introduced in same nucleic acid construct or they can be introduced in separate nucleic acid constructs.

The step of introducing E4ORF1 sequences can be performed using any suitable system known in the art, including, but not limited to, transfection techniques and viral-mediated transduction techniques. Transfection methods that can be used in accordance with the present invention include, but are not limited to, liposome-mediated transfection, polybrene-mediated transfection, DEAE dextran-mediated transfection, electroporation, calcium phosphate precipitation, microinjection, and micro-particle bombardment. Viral-mediated transduction methods that can be used include, but are not limited to, lentivirus-mediated transduction, adenovirus-mediated transduction, retrovirus-mediated transduction, adeno-associated virus-mediated transduction and herpesvirus-mediated transduction.

Any suitable means of transfecting or transducing cells with E4ORF1 nucleic acid sequences can be used. For example, the E4ORF1 nucleic acid sequences can be transfected into cells using standard methods known in the art, including, but not limited to, liposome-mediated transfection, polybrene-mediated transfection, DEAE dextran-mediated transfection, electroporation, calcium phosphate precipitation, microinjection, or micro-particle bombardment. Similarly, the E4ORF1 nucleic acid sequences can be delivered to cells using a viral delivery system such as lentivirus, adenovirus, retrovirus, adeno-associated virus or herpesvirus delivery system. In one embodiment, the E4ORF1 nucleic acid sequences are delivered to cells using a lentiviral gene delivery system.

The present invention also provides vectors, including expression vectors and viral vectors, which contain the E4ORF1 nucleic acid sequences. In some embodiments these sequences are unaccompanied by the entire E4 region. In some embodiments these sequences are unaccompanied by other adenovirus E4ORFs such as E4ORFs 2-6. In one embodiment, the present invention provides a lentivirus vector comprising the E4ORF1 sequence. In one embodiment the present invention provides a lentivirus vector comprising the E4ORF1 sequence unaccompanied by the entire E4 region, or unaccompanied by adenovirus E4ORFs 2, 3, 4, 5 and/or 6

While in some embodiments a nucleotide sequence encoding an E4ORF1 polypeptide (or a variant, derivative, mutant, or fragment thereof), may be used, in other embodiments an E4ORF1 polypeptide (or a variant, derivative, mutant, fragment, or peptidomimetic thereof) may be used. A peptidomimetic is a small protein-like chain designed to mimic a peptide. Such a molecule could be designed to mimic an E4ORF1 polypeptide. Various different ways of modifying a peptide to create a peptidomimetic or otherwise designing a peptidomimetic are known in the art and can be used to create an E4ORF1 peptidomimetic.

The handling, manipulation, and expression of E4ORF1 sequences according to the present invention may be performed using conventional techniques of molecular biology and cell biology. Such techniques are well known in the art. For example, one may refer to the teachings of Sambrook, Fritsch and Maniatis eds., "Molecular Cloning A Laboratory Manual, 2nd Ed., Cold Springs Harbor Laboratory Press, 1989); the series Methods of Enzymology (Academic Press, Inc.), or any other standard texts for guidance on suitable techniques to use in handling, manipulating, and expressing E4ORF1 sequences.

III. COMPOSITIONS

In some embodiments the present invention provides "engineered neural cells" and/or "engineered neural stem or progenitor cells" that comprise a nucleic acid sequence that encodes an adenovirus E4ORF1 polypeptide, or that comprise an adenovirus E4ORF1 polypeptide, and compositions comprising such engineered cells. In those embodiments of the invention that provide engineered neural stem or progenitor cells, such cells may be differentiated to form engineered neural cells (such as engineered neurons or glia). Conversely, in those embodiments of the invention that provide engineered neural cells, such cells may have been derived from neural stem or progenitor cells, such as engineered neural stem or progenitor cells. In some embodiments, the neural cells and/or neural stem or progenitor cells provided herein are mammalian cells, such as human or non-human primate cells, or rabbit, rat, mouse, goat, pig, or other mammalian cells.

As used herein the term "neural cells" refers collectively to both neuronal cells and glial cells. As used herein the terms "neural stem cells" and "neural progenitor cells" are used in accordance with their accepted meanings in the art. While stem cells and progenitor cells differ in their developmental potential (stem cells generally being at least multipotent, while progenitor cells generally have a more limited developmental potential), the terms "neural stem cells" and "neural progenitor cells," as those terms are used herein, are used to refer to cells that have the ability to produce both neuronal cells and glial cells. Some embodiments of the present invention involve neuronal progenitors and glial progenitors. Those terms, as used herein, refer to progenitor cells with more limited potency than neural progenitors— with neuronal progenitors having the ability to produce neuronal cells and glial progenitors having the ability to produce glial cells.

In some embodiments the engineered neural cells (or neural stem or progenitor cells) provided herein are, or are derived from, cells that are gene-modified such that they comprise one or more genetic modifications in addition to and apart from the expression of E4ORF1. For example, such cells may comprise a corrected version of a gene known to be involved in, or suspected of being involved in a disease or disorder that affects neural cells.

The engineered neural cells of the present invention may exist in, or be provided, in various forms. For example, in some embodiments the engineered neural cells may comprise a population of cells, such as an isolated population of cells. In some embodiments the engineered neural cells may comprise a population of cells in vitro. In some embodiments the engineered neural cells may comprise a substantially pure population of cells. For example, in some embodiments at least about 50%, preferably at least about 75-80%, more preferably at least about 85-90%, and most preferably at least about 95% of the cells making up a total cell population will be engineered neural cells of the invention, for example E4ORF1-expressing neural cells, or E4ORF1-expressing neural cells expressing at least one, two, three, or more neural cell markers, neuronal cell markers, or glial cell markers, such as one of the neural, neuronal, or glial cell markers described herein. In some embodiments the engineered neural cells (or engineered neural stem or progenitor cells) may be provided in the form of a composition containing the engineered cells and one or more additional components. For example, in some embodiments the present invention may provide a composition comprising a population of engineered neural cells (or engineered neural stem or progenitor cells) as described herein together with a carrier solution, such as a physiological saline solution, cell suspension medium, cell culture medium, or the like. In some embodiments such compositions may be therapeutic compositions—comprising a population of engineered neural cells (or engineered neural stem or progenitor cells) and a carrier solution that is suitable for administration to a subject, such as a human subject. Other therapeutically acceptable agents can be included if desired. One of ordinary skill in the art can readily select suitable agents to be included in the therapeutic compositions depending on the intended use. In some embodiments the engineered neural cells (or engineered neural stem or progenitor cells) of the invention may be provided in the form of a composition (e.g. a therapeutic composition) that contains the engineered neural cells and one or more additional cell types. Such additional cell types may be, for example, cell types useful in the maintenance or culture of the engineered neural cells (such as "feeder" cells, cells that produce trophic factors, and the like), or cell types intended to be used together with the engineered neural cells—for example for use in an in vitro model system or for use in co-administration to a subject. Examples of such additional cell types include, but are not limited to, other neural cells (such as astrocytes, oligodendrocytes, Schwann cells, and/or neurons), other neural progenitor cells, endothelial cells, and pericytes. Where endothelial cells are used, the endothelial cells may also themselves be engineered to express an E4ORF1 polypeptide. For example, E4ORF1-expressing endothelial cells to be used can be generated as described in U.S. Pat. No. 8,465,732, the contents of which are hereby incorporated by reference.

i. Neuronal Cells

In those embodiments of the present invention that provide or involve neuronal cells, the neuronal cells may be any type of neuronal cell, including central and peripheral neurons. In some embodiments the neuronal cells are hippocampal neurons in particular. In some embodiments the neuronal cells are, or are derived from, primary neuronal cells. In other embodiments, the neuronal cells are derived from stem cells, progenitor cells, or non-neuronal cells. For example, in some embodiments the neuronal cells may be derived from neural stem cells, or neural progenitor cells, or neuronal progenitor cells. In some embodiments the neuronal cells may be derived from pluripotent stem cells, such as embryonic stem cells or induced pluripotent stem cells (iPSCs). Similarly, in some embodiments the neuronal cells may be derived by trans-differentiation from other differentiated cells such as differentiated non-neuronal cells. In some embodiments the neuronal cells are, or are derived from, cells that are gene-modified or comprise one or more genetic modifications in addition to and apart from the expression of E4ORF1. For example, such cells may comprise a corrected version of a gene known to be involved in, or suspected of being involved in a disease or disorder that affects neurons.

In some embodiments, engineered (E4ORF1-expressing) neuronal cells of the invention have an axon length that is (or is about), on average, 10%, 20%, 30%, 40%, 50%, 60%, 70%, 80%, 90%, 100%, 125%, 150%, 175%, 200% or more than 200% greater than that of axons of control neuronal cells. In some embodiments, engineered (E4ORF1-expressing) neuronal cells of the invention have a number of axonal branches per 100 µm of axon that is (or is about), on average, 10%, 20%, 30%, 40%, 50%, 60%, 70%, 80%, 90%, 100%, 125%, 150%, 175%, 200% or more than 200% greater than the number of axonal branches per 100 µm of axon of control neuronal cells. In some embodiments, engineered (E4ORF1-expressing) neuronal cells of the invention have a number of processes per neuron that is (or is about), on average, 10%, 20%, 30%, 40%, 50%, 60%, 70%, 80%, 90%, 100%, 125%, 150%, 175%, 200%, or more than 200% greater than the number of processes per neuron of control neuronal cells. In some embodiments, engineered (E4ORF1- expressing) neuronal cells of the invention have a number of axonal branches that is (or is about), on average, 10%, 20%, 30%, 40%, 50%, 60%, 70%, 80%, 90%, 100%, 125%, 150%, 175%, 200%, or more than 200% greater than the number of axonal branches of control neuronal cells. In some such embodiments, the measurements referred to above are obtained 3, 4, 5, 6, 7, 8, 9, 10, 11, 12, 13, or 14 days after transduction or transfection of the engineered cells with an E4ORF1 sequence. In some such embodiments, the measurements referred to above are obtained using any standard method known in the art for measuring such neuronal characteristics. In some such embodiments, the measurements referred to above are obtained using a method as described in Example 2 herein, or any suitable variant of such method.

Many cell types, including neuronal cell types, tend to lose some of their normal phenotypic characteristics when grown in culture, and particularly when transformed to facilitate their growth in culture. For example when cells are grown in culture they may become less differentiated and/or exhibit a decrease or loss of one or more of their usual phenotypic characteristics. It is a particular advantage of the present invention that the engineered neuronal cells of the invention maintain certain typical neuronal-cell specific phenotypic characteristics even upon expression of adenovirus E4ORF1 sequences therein. For example, in certain embodiments, engineered neuronal cells according to the present invention express one or more markers normally-expressed by one or more subtypes of neuronal cells, including, but not limited to, the pan neuronal markers βIII tubulin, MAP2, tau, NeuN and/or neurofilament. The engineered neuronal cells of the invention may also retain one or more other characteristics of neuronal cells including, but not limited to, lineage identity, morphological/structural characteristics (such as the presence of axons, dendrites, synaptic terminals, synaptic and other connections between neurons, morphological interactions with glial cells, and the like), electrophysiological or other physiological characteristics (including electrical excitability, ion channel activity, neurotransmitter receptor activity, action potential transmission, synaptic transmission, synaptic plasticity, long-term potentiation, and the like), biochemical characteristics (such as expression and/or release of neurotransmitters, expression and/or activation of neurotransmitter receptors, expression of neuronal marker proteins, and the like), and/or any other biological characteristics of neurons known in the art.

ii. Glial Cells

In those embodiments of the present invention that involve glial cells, the glial cells may be astrocytes, oligodendrocytes, ependymal cells, radial glia, Schwann cells, satellite cells, enteric glial cells, or microglial cells. In some embodiments the glial cells are astrocytes in particular. In some embodiments the glial cells are, or are derived from, primary glial cells. In other embodiments, the glial cells are derived from stem cells, progenitor cells, or non-glial cells. For example, in some embodiments the glial cells may be derived from neural stem cells, or neural progenitor cells, or glial progenitor cells. In some embodiments the glial cells may be derived from pluripotent stem cells, such as embryonic stem cells or induced pluripotent stem cells (iPSCs). Similarly, in some embodiments the glial cells may be derived by trans-differentiation from other differentiated cells such as differentiated non-glial cells.

In some embodiments the glial cells are, or are derived from, cells that are gene-modified or comprise one or more genetic modifications in addition to and apart from the expression of E4ORF1. For example, such cells may comprise a corrected version of a gene known to be involved in, or suspected of being involved in a disease or disorder that affects glial cells.

In some embodiments, engineered (E4ORF1-expressing) glial cells of the invention have a proliferation rate that is, or is about, or is at least, or is at least about, on average, 1.5-fold, 2-fold, 3-fold, 4-fold, 5-fold, 6-fold, 8-fold, 10-fold, or more than 10-fold greater than that of control glial cells. In some embodiments, the engineered (E4ORF1-expressing) glial cells of the invention exhibit an increase in cell number at about three weeks following transduction or transfection with E4ORF1 that is, or is about, or is at least, or is at least about, 4-fold, 5-fold, 6-fold, or more than 6-fold greater than the increase in cell number in control glial. In some embodiments, engineered (E4ORF1-expressing) glial cells of the invention can be maintained in culture for more than 2, more than 3, or more preferably more than 4, 5, 6, 7, 8, 9, or 10 passages while still maintaining high viability and/or while continuing to maintain a glial phenotype (for example as determined by morphology and/or expression of glial markers, such as glial fibrillary acidic protein (GFAP) in the case of astrocytes. In some embodiments, the engineered (E4ORF1-expressing) glial cells of the invention can be maintained in culture for a greater number of passages without a significant decrease in viability and/or without significant loss of the glial phenotype (for example as determined by morphology and/or expression of glial markers, such as GFAP) as compared to control glial cells. In some such embodiments, the measurements of proliferation rates and cell numbers, and assessment of passaging success in the glial cells, may be performed using any standard methods known in the art for measuring/assessing such characteristics. In some such embodiments, the measurements referred to above are obtained using a method as described in Example 1 herein, or any suitable variant of such method.

It is a particular advantage of the present invention that the engineered glial cells of the invention maintain certain typical glial-cell specific phenotypic characteristics even upon expression of adenovirus E4ORF1 sequences therein. For example, in certain embodiments, engineered glial cells according to the present invention express one or more markers normally expressed by one or more subtypes of glial cells, including, but not limited to, glial fibrillary acid protein (GFAP), glial cell-derived neurotrophic factor (GDNF), and GLT-1. For example, in embodiments where the glial cells are astrocytes, the glial cells may express GFAP. The engineered glial cells of the invention may also retain one or more other phenotypic characteristics typical of glial cells. For example, in the case of engineered astrocytes, the phenotypic characteristics that may be maintained include, but are not limited to, morphological/structural characteristics (such as the typical star-like branching morphology of astrocytes, association with neuronal synapses, "vascular feet" that connect astrocytes to capillary walls, and the like), electrophysiological and other physiological characteristics (including ion channel activity, regulation of ion concentration in the extracellular space, and the like), biochemical characteristics (such as expression and/or release and/or uptake of neurotransmitters such as glutamate, expression of astrocyte marker proteins, metabolic support to neurons, and the like), neuronal guidance, formation of glial scar tissue, and/or any other biological characteristics of astrocytes known in the art.

IV. METHODS AND APPLICATIONS

The engineered neural cells and/or engineered neural stem or progenitor cells provided by the present invention have certain properties that can make them useful in a variety of different applications. Similarly, the methods provided herein for making such engineered neural cells and/or engineered neural stem or progenitor cells can be used in a variety of different settings. In general, the engineered neural cells and neural stem or progenitor cells provided herein can be used for any application in which non-engineered (i.e. non-E4OFR1-expressing) neural cells or neural stem or progenitor cells are currently used or could be used. For example, in the case of engineered neural stem or progenitor cells, such cells may be used for any applications for which neural stem or progenitor cells are currently used or could be used (including, but not limited to, for research purposes and/or for therapeutic purposes, such as for transplantation into a subject for regenerative therapy, for example for treatment of Parkinson's diseases, Huntington's disease, multiple sclerosis of other diseases or disorders affecting the nervous system), or may be used to generate a population of engineered differentiated neural cells, which may then in turn be used for any applications for which differentiated neural cells are currently used or could be used, including, but not limited to, for research purposes and for therapeutic purposes—similarly to the uses described above for neural stem and progenitor cells.

The increased cellular proliferation rates and passage numbers exhibited by E4ORF1-expressing glial cells as compared to control (i.e. non-E4ORF-1 expressing) glial cells can make it advantageous to use the engineered glial cells of the present invention in place of other glial cells in a variety of methods including, methods for generating or maintaining cultures of glial cells, methods for deriving glial cells from stem or progenitor cells, methods of deriving glial cells from differentiated non-glial cells (e.g. by transdifferentiation), basic scientific research applications, target discovery applications, drug discovery applications, and drug efficacy, toxicity, and/or safety testing applications. In some embodiments, the engineered glial cells of the invention may be used in co-culture methods—for example involving co-culture of glial cells with neuronal cells. In some embodiments, the engineered glial cells of the invention may be used in disease models, or other biological model systems, such as blood-brain-barrier model systems. Furthermore, in some embodiments engineered glial cells may be useful in therapeutic applications for which non-engineered glial cells are used or could be used, including, but not limited to, in vivo cell transplantation procedures, for example for regenerative medicine applications. For example, in some embodiments engineered glial cells or neural stem or progenitor cells may be generated or used in connection with an in vivo transplantation procedures, for example to treat a disease, disorder or condition associated with a glial cell defect, a glial cell deficiency, or glial cell damage. Examples of such diseases, disorders and conditions include, but are not limited to, those associated with traumatic brain injury, spinal cord injury, neurodegenerative diseases, neurodevelopmental diseases, and diseases associated with demyelination or dysmyelination of neurons, including, but not limited to, multiple sclerosis (MS), post viral acute demyelination, transverse myelitis, chronic inflammatory demyelinating polyneuropathy (CIDP), Guillain-Barre Syndrome, progressive multifocal leukoencephalopathy (PML), leukodystrophies, adrenoleukodystrophy, Krabbe leukodystrophy, metachromatic leukodystrophy, Alexander disease, Canavan disease, Cockayne syndrome, and Pelizaeus-Merzbacher disease.

Similarly, the increased axon length, increased numbers of minor processes, and increased number of branches per axon exhibited by E4ORF1-expressing neuronal cells as compared to control (i.e. non-E4ORF-1 expressing) neuronal cells can make it advantageous to use the engineered neuronal cells (or neural stem of progenitor cells that can become engineered neuronal cells) of the invention in place of other neuronal cells (or neural stem of progenitor cells) in a variety of methods, including methods for generating or maintaining cultures of neuronal cells, methods for deriving neuronal cells from stem or progenitor cells, methods of deriving neuronal cells from differentiated non-neuronal cells (e.g. by transdifferentiation), basic scientific research applications, target discovery applications, drug discovery applications, and drug efficacy, toxicity, and/or safety testing applications. In some embodiments, the engineered neuronal cells of the invention may be used in co-culture methods—for example involving co-culture of glial cells with neuronal cells. In some embodiments, the engineered neuronal cells of the invention may be used in disease models, or other biological model systems, such as blood-brain-barrier model systems. Furthermore, in some embodiments the engineered neuronal cells (or neural stem of progenitor cells that can become engineered neuronal cells) may be useful in therapeutic applications for which non-engineered neuronal cells or neuronal stem or progenitor cells are used or could be used, including, but not limited to, regenerative medicine applications. For example, in some embodiments the engineered neuronal cells or neural stem or progenitor cells may be used in an in vivo transplantation procedure, for example to treat a disease, disorder or condition associated with a neuronal cell defect, a neuronal cell deficiency, or neuronal cell damage. Examples of such diseases, disorders and conditions include, but are not limited to, those associated with traumatic brain injury, spinal cord injury, neurodegenerative diseases and neurodevelopmental diseases, including, but not limited to Alzheimer's Disease, Parkinson's Disease, Huntington's disease, and amyotrophic lateral sclerosis (ALS).

As mentioned above, in some embodiments the engineered cells of the present invention can be used in various therapeutic applications. Thus, in some aspects, the present invention provides various therapeutic methods, such as methods for treating subjects in need thereof by administering to such subjects an effective amount of engineered E4ORF1-expressing neural cells (or of a composition comprising engineered E4ORF1-expressing neural cells), or an effective amount of engineered neural stem or progenitor cells. In such treatment methods, the cells can be administered to subjects using any suitable means known in the art. For example, the cells can be administered by injection or infusion into the blood stream or tissue at a desired location. For example, in the case of treatment of diseases, disorders, or conditions of the nervous system, engineered cells according to the present invention may be administered directly into, or in the vicinity of, the affected areas of the nervous system. In the case of treatment of specific neural injuries or specific neural lesions, the cells may be administered directly into, or in the vicinity of, the site of the injury or lesion, for example the site of a spinal cord injury or lesion. In some embodiments the engineered neural cells (or engineered neural stem or progenitor cells) of the invention may administered together with one or more additional cell types. Such additional cell types may be, for example, cell types useful for supporting the maintenance or survival of the engineered neural cells (such as "feeder" cells, cells that produce trophic factors, and the like), and/or cell types that may provide some additional therapeutic benefit. Examples of such additional cell types include, but are not limited to, other neural cells (such as astrocytes, oligodendrocytes, Schwann cells, and/or neurons), other neural progenitor cells, endothelial cells, and pericytes. Where endothelial cells are to be used, the endothelial cells may also themselves be engineered to express an E4ORF1 polypeptide. Such E4ORF1-expressing endothelial can be generated as described in U.S. Pat. No. 8,465,732, the contents of which are hereby incorporated by reference. The engineered cells can be administered in a single dose or in multiple doses. The skilled artisan will be able to select a suitable method of administration according and a suitable dosing regimen depending on the desired use.

Similarly, in other embodiments engineered cells of the present invention can be created in vivo in various therapeutic applications. Thus, in some aspects, the present invention provides various therapeutic methods, such as methods for treating subjects in need thereof, which comprise administering to such subjects an effective amount of an E4ORF1-encoding nucleotide sequence (for example in a suitable vector, and/or under the control of a suitable promoter) such that neural cells in the subject are transfected or transduced with the E4ORF1 sequence and become engineered neural cells in vivo. In such treatment methods, the nucleotide molecules can be administered to subjects using any suitable means known in the art. For example, the nucleotide molecules (for example in a suitable vector) can be administered by injection or infusion into the blood stream or tissue at a desired location. For example, in the case of treatment of diseases, disorders, or conditions of the nervous system, the nucleic acid molecules may be administered directly into, or in the vicinity of, the affected areas of the nervous system. In the case of treatment of specific neural injuries or specific neural lesions, the nucleic acid molecules may be administered directly into, or in the vicinity of, the site of the injury or lesion, for example the site of a spinal cord injury or lesion. The nucleic acid molecules can be administered in a single dose or in multiple doses. The skilled artisan will be able to select a suitable method of administration according and a suitable dosing regimen depending on the desired use.

Many neural cells are notoriously difficult to grow or maintain in culture without immortalization or without the use of feeder cells. Through expression of adenovirus E4ORF1 in such cells, the present invention can provide a means to facilitate the culture of such cell types—without compromising the cells' phenotypic integrity or lineage identity. For example, it is a particular advantage of the present invention that engineered E4ORF1-expressing neural cells have certain features that may facilitate cell culture or may result in the generation of superior cell cultures. For example, engineered glial cells of the invention have higher proliferation rates than control glial cells, and engineered glial cells have certain enhanced morphological features as compared to control neural cells. Methods of culturing cells are well known in the art and any suitable cell culture methods can be used. For example, the engineered glial cells of the invention can be cultured using methods known to be useful for culturing non-engineered glial cells and the engineered neuronal cells of the invention can be cultured using methods known to be useful for culturing non-engineered neuronal cells. In some embodiments cell culture can be performed in the absence of serum, or in the absence of exogenous growth factors, or in the absence of both serum and exogenous growth factors. The engineered cells of the invention can also be cryopreserved. One of skill in the art can readily culture and cryopreserve cells, such as the E4ORF1-expressing neural cells of the invention, using methods known to those skilled in the art, such as the methods described in Culture of Animal Cells: A Manual of Basic Technique, 4th Edition (2000) by R. Ian Freshney ("Freshney"), the contents of which are hereby incorporated by reference.

In some embodiments, the present invention provides feeder cells, conditioned medium, and cell products that comprise, or are derived from, engineered neural cells of the invention and that can be useful to support the survival or growth of other cells, such as other neural cells (including non-engineered neural cells). For example, in one embodiment a population of engineered glial cells can be used as feeder cells to support the growth of neurons, or a population of engineered neuronal cells can be used as feeder cells to support the growth of glial cells. Similarly, in other embodiments the present invention may provide conditioned cell culture medium obtained from a culture of engineered neural cells of the invention, or cell products (such as total cell lysates, cell fractions, or specific cell products) obtained from a culture of engineered neural cells of the invention.

In some embodiments the present invention provides a co-culture method for culturing a population of neurons, the method comprising: culturing a population of neurons and a population of engineered glial cells together in the same culture vessel, wherein the engineered glial cells contain a nucleotide sequence that encodes an adenovirus E4ORF1 polypeptide or contain an adenovirus E4ORF1 polypeptide. In some such embodiments the engineered glial cells form a feeder cell layer on a surface of the culture vessel, and the neurons may be placed on the feeder cell layer. In another embodiment the present invention provides a method of culturing neurons comprising: contacting a population of neurons with glial-cell conditioned medium, wherein the glial-cell conditioned medium is obtained from a culture of engineered glial cells, and wherein the engineered glial cells contain a nucleotide sequence that encodes an adenovirus E4ORF1 polypeptide or contain an adenovirus E4ORF1 polypeptide. Similarly, in another embodiment the present invention provides a method of culturing neurons comprising: (a) obtaining a population of engineered glial cells, wherein the engineered glial cells contain a nucleotide sequence that encodes an adenovirus E4ORF1 polypeptide or contain an adenovirus E4ORF1 polypeptide, (b) culturing the engineered glial cells in a culture vessel, (c) collecting conditioned medium from the culture vessel, (d) adding the conditioned medium to a culture of neurons, and (e) culturing the neurons. In some embodiments the present invention also provides conditioned cell culture medium obtained from a culture of engineered glial cells, wherein the engineered glial cells contain a nucleotide sequence that encodes an adenovirus E4ORF1 polypeptide or contain an adenovirus E4ORF1 polypeptide.

In some embodiments the engineered neural cells of the present invention may be useful in an in vitro blood brain barrier model system. For example, such a system may comprise a population of engineered glial cells, wherein the engineered glial cells contain a nucleotide sequence that encodes an adenovirus E4ORF1 polypeptide or contain an adenovirus E4ORF1 polypeptide. Similarly, in some embodiments the present invention provides an in vitro blood brain barrier model system or kit comprising: (a) a population of engineered glial cells, wherein the engineered glial cells contain a nucleotide sequence that encodes an adenovirus E4ORF1 polypeptide or contain an adenovirus E4ORF1 polypeptide, (b) pericytes, and (c) endothelial cells. In each of such embodiments the engineered glial cells may be astrocytes.

V. KITS

The present invention also provides kits for carrying out the various methods described herein and/or for producing the engineered cells provided herein. Such kits may contain any of the components described herein, including, but not limited to, E4ORF1 sequences (for example in a vector), neural cells (such as neurons or glia), populations of engineered neural cells (such as engineered neurons or glia), control non-engineered neural cells, sample/standard engineered neural cells, means or compositions for detection of E4ORF1 sequences or E4ORF1 polypeptides (e.g. nucleic acid probes, antibodies, etc.), media or compositions useful for maintaining or expanding neural cells or engineered neural cells, media conditioned by engineered glial cells, means or compositions for administering engineered neural cells to a subject, or any combination thereof. In some embodiments the present invention provides kits comprising engineered glial cells, such as astrocytes, for use in an in vitro blood brain barrier model system. For example, in one embodiment the present invention provides a kit comprising a population of engineered astrocytes as described herein as well as pericytes and endothelial cells. All such kits may optionally comprise instructions for use, containers, culture vessels and the like. A label may accompany the kit and may include any writing or recorded material, which may be electronic or computer readable form (e.g., disk, optical disc, memory chip, or tape) providing instructions or other information for use of the kit contents.

Certain aspects of the present invention may be further described in the following non-limiting Examples.

EXAMPLES

Example 1: Generation and Characterization of E4ORF1-Expressing Astrocytes

Methods. 10-12 P1 postnatal mouse pups were sacrificed, and the brains were isolated into dissection medium. The two cerebral hemispheres were tweezed apart and the meninges and the olfactory bulbs were carefully removed. Fine scissors were used to mince the tissues into small pieces (about 0.5 mm diameter). The small tissue pieces were collected and transferred with the dissection medium into a 15 ml conical tube. The tissue pieces were allowed to settle (~1-2 minutes), and were then removed from the dissection medium carefully. 6-8 ml of TrypLE was added to the conical tube and the cap closed tightly. The tube was flipped up and down 3 times followed by placing the tube in a water bath at 37° C. for 15 minutes, while swirling the tube occasionally. The TrypLE was then removed without disturbing the diced tissue and 1-2 ml of astrocyte culture medium was added. DNAse was added for 1 minute while agitating the tube by frequent tapping. The tissue pieces were then rinsed with astrocyte culture medium 3 times. The tissue pieces were then triturated in ~1 ml of astrocyte culture medium by passing the tissue pieces and medium up and down 15 times through a plastic P1000 pipette tip, followed by triturating the tissue and medium once using a flame polished glass pipette. The triturated cell suspension was then centrifuged for 5 minutes at 400 g and the supernatant was then removed. The cell pellet was resuspended in 5 ml astrocyte culture medium, before plating the cells on a T25 flask and then incubating them in a regular cell culture incubator. The medium was replaced with fresh astrocyte culture medium every day for 6 days after firmly patting the flasks 5-8 times to remove weakly adherent non-astroglial cells. On day 7, the cells were transduced with E4ORF1 lentivirus (40-50 μl concentrated virus) using polybrene (8 ng/ml, medium without antibiotics). After 24 hours the infection medium was replaced with regular astrocyte culture medium. The cells were passaged upon reaching confluence.

Materials. P1 B6 postnatal mouse pups were used. The dissection medium was L15 medium supplemented with 1× B27 supplement and 1× penicillin/streptomycin. The astrocyte culture medium was MEM Medium supplemented with 10% horse serum, 0.6% glucose, 1× GlutaMax, and 1× penicillin/streptomycin. T25/T75 culture flasks, TrypLE/Accutase, and DNAse were also used.

Results. One week after E4ORF1 transduction the E4ORF1-expressing astrocytes exhibited a 3-5 fold increase in cell numbers as compared to control astrocytes that were not transduced with E4ORF1. By three weeks after E4ORF1 transduction the E4ORF1-expressing astrocytes exhibited a 5-6 fold increase in cell numbers as compared to the control astrocytes. The E4ORF1 astrocyte cells were also able to be passaged for larger numbers of population doublings than controls without any detrimental effects noted. The E4ORF1 astrocytes maintained high viability after 4 passages, and appeared to maintain their astroglial phenotype—they expressed glial fibrillary acidic protein (GFAP) and their morphology and morphological heterogeneity was comparable to that of the control cells. Neither NG2 nor CD31 expression was detected.

Example 2: Generation and Characterization of E4ORF1-Expressing Neurons

Methods. Embryonic day 18 (E18) mouse embryos were sacrificed, and the brains were isolated into dissection medium. The two cerebral hemispheres were tweezed apart and the meninges and the olfactory bulbs were carefully removed. The hippocampi were carefully isolated from the hemispheres. Fine scissors were used to mince the tissues into small pieces (about 0.5 mm diameter). The small tissue pieces were collected and transferred with the dissection medium into a 15 ml conical tube. The tissue pieces were allowed to settle (~1-2 minutes), and were then removed from the dissection medium carefully. 6-8 ml of TrypLE was added to the conical tube and the cap closed tightly. The tube was flipped up and down 3 times followed by placing the tube in a water bath at 37° C. for 15 minutes, while swirling the tube occasionally. The TrypLE was then removed without disturbing the diced tissue and 1-2 ml of neuronal plating medium was added. DNAse was added for 1 minute while agitating the tube by frequent tapping. The tissue pieces were then rinsed with neuronal plating medium 3 times. The tissue pieces were then triturated in ~1 ml of neuronal plating medium by passing the tissue pieces and medium up and down 10 times through a plastic P1000 pipette tip, followed by triturating the tissue and medium once using a flame polished glass pipette. The triturated cell suspension was then centrifuged for 5 minutes at 400 g and the supernatant was then removed. The cell pellet was resuspended in 5 ml neuronal plating medium, before plating the cells on poly-L-lysine coated surface of 24 well plates or on polylysine coated glass coverslips (100,000 per coverslip in a well a 24-well plate) and then incubating them in a regular cell culture incubator. The next day (day 3), the cells were transduced with E4ORF1 lentivirus (2 μl concentrated virus) or with E4ORF1 lentivirus along with turboGFP lentivirus (Evrogen Inc., 5-10 μl concentrated virus in total) using polybrene (8 μg/ml, medium without antibiotics). Neurons transduced with only turboGFP served as controls. After 16 or 24 hours the infection medium was replaced with regular neuronal plating medium or with neuronal plating medium plus laminin (0.01 mg/ml). Half of the volume of the culture medium was changed every 4-5 days. Cells to be used for imaging were kept for 4-5 days before fixation and imaging by confocal microscopy.

Materials. E18 pregnant B6 mouse. The dissection medium was L15 medium supplemented with 1× B27 supplement and 1× penicillin/streptomycin. The plating medium was Neurobasal Medium supplemented with 5% FBS, 0.6% glucose, 1× GlutaMax, and 1× penicillin/streptomycin, 1× B27 supplement. 24 well plates which were coated with poly-L-lysine (1 mg/ml), TrypLE, and DNAse were also used.

Figure 2:
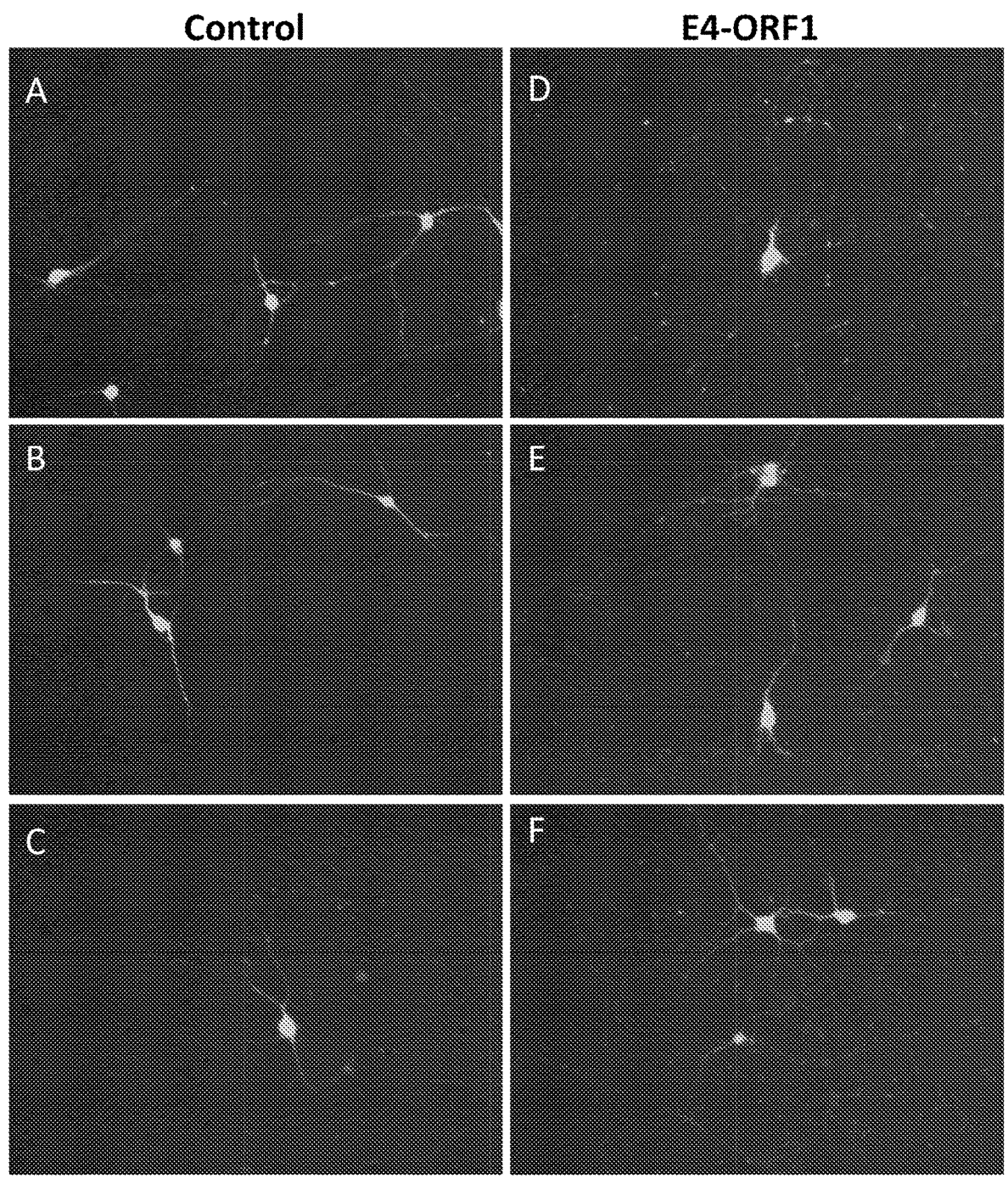
FIG. 2. Exemplary fluorescence microscopy images of control (FIGS. 2A, 2B, and 2C) and E4ORF1-expressing hippocampal neurons (FIGS. 2D, 2E, and 2F). Neurons in both the control and E4ORF1 groups express green fluorescent protein (GFP). The resulting green fluorescence appears light/white (against a dark background) in the gray-scale versions of the images provided herein.

Results. Neurons expressing E4ORF1 were found to have increased axon lengths as compared to neurons not expressing E4ORF1 (average axon length of 1254.5±137.2 μm as compared to 835.3±146.2 μm in controls) (see FIG. 1A), increased minor process number per neuron as compared to neurons not expressing E4ORF1 (5.73±0.43 per neuron as compared to 4.04±0.38 per neuron in controls) (see FIG. 1B), and increased number of primary axonal branches per axon as compared to neurons not expressing E4ORF1 (6.74±0.71 as compared to 2.91±0.33 in the control group) (see FIG. 1C). These differences were all statistically significant ($p<0.05$). Tables 1, 2, 3, and 4 below provide some additional data from these experiments. Engineered (E4ORF1-expressing) hippocampal neurons were found to maintain a typical neuronal morphology and expressed pan neuronal markers such as βIII tubulin, MAP2, tau, NeuN and neurofilament. FIG. 2 provides some illustrative microscopy images of control (FIGS. 2A, 2B, and 2C) and E4ORF1-expressing neurons (FIGS. 2D, 2E, and 2F).

TABLE 1

Characteristics of E4ORF1-Expressing Neurons

| Axon length (μm) | Axonal branches | Process number | Branches per 100 μm of axon |
|---|---|---|---|
| 1746 | 8 | 5 | 0.46 |
| 1359 | 10 | 7 | 0.74 |
| 2003 | 12 | 5 | 0.60 |
| 1393 | 5 | 7 | 0.36 |
| 1535 | 3 | 4 | 0.20 |
| 359 | 11 | 9 | 3.06 |
| 552 | 7 | 11 | 1.27 |
| 1324 | 7 | 10 | 0.53 |
| 2138 | 17 | 5 | 0.80 |
| 943 | 6 | 5 | 0.64 |
| 1217 | 9 | 3 | 0.74 |
| 736 | 8 | 6 | 1.09 |
| 1161 | 6 | 7 | 0.52 |
| 2407 | 3 | 5 | 0.12 |
| 845 | 5 | 4 | 0.59 |
| 1568 | 7 | 7 | 0.45 |
| 379 | 3 | 6 | 0.79 |
| 2529 | 5 | 5 | 0.20 |
| 2036 | 4 | 3 | 0.20 |
| 731 | 6 | 1.5 | 0.82 |
| 677 | 6 | 5 | 0.89 |
| 853 | 3 | 4 | 0.35 |
| 362 | 4 | 4 | 1.10 |
| Mean 1254.48 | Mean 6.74 | Mean 5.74 | Mean 0.72 |

TABLE 2

Characteristics of Control (Non-E4ORF1-Expressing) Neurons

| Axon length (μm) | Axonal branches | Process number | Branches per 100 μm of axon |
|---|---|---|---|
| 1555 | 4 | 8 | 0.26 |
| 773 | 2 | 4 | 0.26 |
| 1649 | 4 | 5 | 0.24 |
| 2741 | 3 | 6 | 0.11 |
| 443 | 3 | 4 | 0.68 |
| 205 | 1 | 5 | 0.49 |
| 573 | 4 | 4 | 0.70 |
| 316 | 1 | 5 | 0.32 |
| 245 | 2 | 2 | 0.82 |
| 1395 | 3 | 1 | 0.22 |
| 458 | 1 | 6 | 0.22 |
| 936 | 2 | 4 | 0.21 |
| 318 | 4 | 3 | 1.26 |
| 344 | 2 | 1 | 0.58 |
| 2417 | 7 | 3 | 0.29 |
| 421 | 3 | 5 | 0.71 |
| 851 | 5 | 3 | 0.59 |
| 249 | 1 | 4 | 0.40 |
| 1026 | 3 | 3 | 0.29 |
| 1106 | 4 | 4 | 0.36 |
| 620 | 1 | 3 | 0.16 |
| 210 | 2 | 2 | 0.95 |
| 361 | 5 | 8 | 1.39 |
| Mean 835.30 | Mean 2.91 | Mean 4.04 | Mean 0.50 |

TABLE 3

Characteristics of E4ORF1 vs. Control Neurons

| | E4ORF1 axon length | Control axon length | E4ORF1 process number | Control process number |
|---|---|---|---|---|
| Mean | 1254.5 | 835.3 | 5.7 | 4.0 |
| Standard Error | 137.2 | 146.2 | 0.4 | 0.4 |
| Median | 1217.0 | 573.0 | 5.0 | 4.0 |
| Mode | #N/A | #N/A | 5.0 | 4.0 |
| Standard Deviation | 658.1 | 701.2 | 2.1 | 1.8 |
| Sample Variance | 433118.1 | 491721.0 | 4.3 | 3.4 |
| Kurtosis | −0.8 | 1.8 | 1.0 | 0.3 |
| Skewness | 0.4 | 1.5 | 1.1 | 0.5 |
| Range | 2170.0 | 2536.0 | 8.0 | 7.0 |
| Minimum | 359.0 | 205.0 | 3.0 | 1.0 |
| Maximum | 2529.0 | 2741.0 | 11.0 | 8.0 |
| Sum | 28853.0 | 19212.0 | 132.0 | 93.0 |
| Count | 23.0 | 23.0 | 23.0 | 23.0 |

TABLE 4

Additional Characteristics of E4ORF1 vs. Control Neurons

| | E4ORF1 branches per 100 μm of axon | Control branches per 100 μm of axon | E4ORF1 axonal branches | Control axonal branches |
|---|---|---|---|---|
| Mean | 0.72 | 0.50 | 6.74 | 2.91 |
| Standard Error | 0.12 | 0.07 | 0.70 | 0.33 |
| Median | 0.60 | 0.36 | 6.00 | 3.00 |
| Mode | #N/A | #N/A | 3.00 | 4.00 |
| Standard Deviation | 0.60 | 0.35 | 3.39 | 1.56 |
| Sample Variance | 0.36 | 0.12 | 11.48 | 2.45 |
| Kurtosis | 11.10 | 1.01 | 2.55 | 0.48 |
| Skewness | 2.91 | 1.25 | 1.39 | 0.70 |

TABLE 4-continued

Additional Characteristics of E4ORF1 vs. Control Neurons

|  | E4ORF1 branches per 100 µm of axon | Control branches per 100 µm of axon | E4ORF1 axonal branches | Control axonal branches |
|---|---|---|---|---|
| Range | 2.94 | 1.28 | 14.00 | 6.00 |
| Minimum | 0.13 | 0.11 | 3.00 | 1.00 |
| Maximum | 3.06 | 1.39 | 17.00 | 7.00 |
| Sum | 16.50 | 11.49 | 155.00 | 67.00 |
| Count | 23.00 | 23.00 | 23.00 | 23.00 |

The present invention is further described by the following claims.

We claim:

1. A substantially pure isolated population of engineered neural cells, engineered neural stem cells, or engineered neural progenitor cells, wherein the engineered neural cells, the engineered neural stem cells, or the engineered neural progenitor cells:
   a. comprise a nucleic acid sequence that encodes an adenovirus E40RF1 polypeptide wherein the nucleic acid is operably linked to a promoter,
   b. do not comprise an entire adenovirus E4 region, and
   c. do not comprise any E4ORF2, E4ORF3, E4ORF4, E4ORF5 or E4ORF6 coding sequences or amino acid sequences.

2. The population of claim 1, wherein the engineered neural cells are engineered neuronal cells or engineered glial cells.

3. The population of claim 2, wherein the engineered neuronal cells are engineered hippocampal neurons.

4. The population of claim 2, wherein the engineered neuronal cells express one or more markers selected from the group consisting of βIII tubulin, MAP2, tau, NeuN and neurofilament.

5. The population of claim 2, wherein the engineered glial cells are selected from the group consisting of engineered astrocytes, engineered oligodendrocytes, engineered ependymal cells, engineered radial glia, engineered Schwann cells, engineered satellite cells, and engineered enteric glial cells.

6. The population of claim 2, wherein the engineered glial cells express one or more markers selected from the group consisting of glial fibrillary acid protein (GFAP), glial cell-derived neurotrophic factor (GDNF), and GLT-1.

7. The population of claim 1, wherein the engineered neural cells are engineered primary neural cells.

8. The population of claim 1, wherein the engineered neural cells, the engineered neural stem cells, or the engineered neural progenitor cells are mammalian cells.

9. The population of claim 1, wherein the engineered neural cells, the engineered neural stem cells, or the engineered neural progenitor cells are human cells.

10. A composition comprising the cell population of claim 1 and a carrier solution.

11. A method of producing a population of the engineered neural cells, the engineered neural stem cells, or the engineered neural progenitor cells according to claim 1, the method comprising: introducing the nucleic acid molecule encoding the adenovirus E4ORF1 protein into one or more neural cells, neural stem cells, or neural progenitor cells, wherein the nucleic acid is operably linked to a promoter thereby producing the engineered neural cells, the engineered neural stem cells, or the engineered neural progenitor cells.

12. The population of claim 1, wherein the engineered neural cells, the engineered neural stem cells, or the engineered neural progenitor cells comprise the adenovirus E4ORF1 polypeptide.

13. The population of claim 1, wherein the nucleic acid sequence is in a viral vector.

14. The population of claim 13, wherein the viral vector is a lentiviral vector, a retroviral vector, an adeno-associated virus vector, or a herpesvirus vector.

15. An in vitro blood brain barrier model system comprising endothelial cells and a population of engineered glial cells, wherein the engineered glial cells:
   (a) comprise a nucleic acid sequence that encodes an adenovirus E40RF1 polypeptide wherein the nucleic acid is operably linked to a promoter,
   (b) do not comprise an entire adenovirus E4 region, and
   (c) do not comprise any E4ORF2, E4ORF3, E4ORF4, E4ORF5 or E4ORF6 coding sequences or amino acid sequences.

16. The system of claim 15, wherein the engineered glial cells are engineered astrocytes.

17. The in vitro blood brain barrier model system of claim 15, further comprising pericytes.

18. The in vitro blood brain barrier model system of claim 15, wherein the engineered glial cells comprise the adenovirus E4ORF1 polypeptide.

19. The in vitro blood brain barrier model system of claim 15, wherein the nucleic acid sequence is in a viral vector.

20. The in vitro blood brain barrier model system of claim 19, wherein the viral vector is a lentiviral vector, a retroviral vector, an adeno-associated virus vector, or a herpesvirus vector.

21. An in vitro composition comprising neural cells and a carrier solution for delivery to a subject, wherein at least 75% of the neural cells in the composition are engineered neural cells that comprise a nucleic acid sequence that encodes an adenovirus E40RF1 polypeptide, do not comprise an entire adenovirus E4 region, and do not comprise any E40RF2, E40RF3, E40RF4, E40RF5 or E40RF6 coding sequences or amino acid sequences.

22. The composition of claim 21, wherein at least 85% of the neural cells in the composition are the engineered neural cells.

23. The composition of claim 21, wherein at least 95% of the neural cells in the composition are the engineered neural cells.

24. The composition of claim 21, wherein the engineered neural cells are engineered neuronal cells.

25. The composition of claim 24, wherein the engineered neuronal cells express one or more markers selected from the group consisting of βIII tubulin, MAP2, tau, NeuN and neurofilament.

26. The composition of claim 24, wherein the engineered neuronal cells are hippocampal neurons.

27. The composition of claim 21, wherein the engineered neural cells are engineered glial cells.

28. The composition of claim 27, wherein the engineered glial cells are selected from the group consisting of engineered astrocytes, engineered oligodendrocytes, engineered ependymal cells, engineered radial glia, engineered Schwann cells, engineered satellite cells, and engineered enteric glial cells.

29. The composition of claim 27, wherein the engineered glial cells express one or more markers selected from the group consisting of glial fibrillary acid protein (GFAP), glial cell-derived neurotrophic factor (GDNF), and GLT-1.

30. The composition of claim 21, wherein the engineered neural cells are mammalian cells.

31. The composition of claim 21, wherein the engineered neural cells are human cells.

32. The composition of claim 21, wherein the nucleic acid sequence is in a viral vector.

33. The composition of claim 32, wherein the viral vector is a lentiviral vector, a retroviral vector, an adeno-associated virus vector, or a herpesvirus vector.

34. A method for culturing a population of neurons, the method comprising either: (a) culturing the population of neurons and a population of engineered glial cells together in the same culture vessel, wherein the engineered glial cells contain a nucleotide sequence that encodes an adenovirus E4ORF1 polypeptide or contain an adenovirus E4ORF1 polypeptide, or (b) contacting the population of neurons with glial-cell conditioned medium, wherein the glial-cell conditioned medium is obtained from a culture of the engineered glial cells thereby culturing the population of neurons.

35. The method of claim 34, wherein in (a) the engineered glial cells are a feeder cell layer on a surface of the culture vessel.

36. The method of claim 35, wherein the population of neurons are placed on the feeder cell layer.

* * * * *